United States Patent [19]

Nguyen

[11] Patent Number: 5,690,961

[45] Date of Patent: Nov. 25, 1997

[54] ACIDIC POLYSACCHARIDES CROSSLINKED WITH POLYCARBOXYLIC ACIDS AND THEIR USES

[75] Inventor: Tuyen T. Nguyen, Wilmington, Del.

[73] Assignee: Hercules Incorporated, Wilmington, Del.

[21] Appl. No.: 362,689

[22] Filed: Dec. 22, 1994

[51] Int. Cl.$^6$ .............. A61K 47/36; C08L 5/00; C08J 3/24; C08K 5/092

[52] U.S. Cl. .......... 424/488; 424/78.3; 424/499; 424/443; 424/423; 525/54.2; 525/937; 514/54; 514/777; 252/315.3; 428/289

[58] Field of Search ............... 424/488, 78.3; 525/54.2; 514/54; 536/123.1

[56] References Cited

U.S. PATENT DOCUMENTS

| | | | |
|---|---|---|---|
| 4,046,779 | 9/1977 | Puskas et al. | 528/188 |
| 4,152,170 | 5/1979 | Nagase et al. | 106/162 |
| 4,487,865 | 12/1984 | Balazs et al. | 524/29 |
| 4,500,676 | 2/1985 | Balazs et al. | 525/54.2 |
| 4,582,865 | 4/1986 | Balazs et al. | 524/29 |
| 4,605,691 | 8/1986 | Balazs et al. | 524/27 |
| 4,636,524 | 1/1987 | Balazs et al. | 514/781 |
| 4,713,448 | 12/1987 | Balazs et al. | 536/55.1 |
| 4,716,154 | 12/1987 | Mälson et al. | 514/54 |
| 4,716,224 | 12/1987 | Sakurai et al. | 536/55.1 |
| 4,772,419 | 9/1988 | Mälson et al. | 252/315.1 |
| 4,795,741 | 1/1989 | Leshchiner et al. | 514/21 |
| 4,851,513 | 7/1989 | Devorg et al. | 523/113 |
| 4,851,521 | 7/1989 | della Valle et al. | 536/55.1 |
| 4,863,907 | 9/1989 | Sakurai et al. | 514/56 |
| 4,886,787 | 12/1989 | deBelder et al. | 514/57 |
| 4,957,744 | 9/1990 | della Valle et al. | 424/401 |
| 4,997,906 | 3/1991 | Thaler et al. | 528/272 |
| 5,008,253 | 4/1991 | Casu et al. | 514/54 |
| 5,099,013 | 3/1992 | Balazs et al. | 536/55.1 |
| 5,128,326 | 7/1992 | Balazs et al. | 514/54 |
| 5,166,331 | 11/1992 | della Valle et al. | 536/55.1 |
| 5,191,016 | 3/1993 | Yalpani | 525/54.2 |
| 5,202,431 | 4/1993 | della Valle et al. | 536/55.1 |
| 5,246,698 | 9/1993 | Leshchiner et al. | 424/78.08 |
| 5,356,883 | 10/1994 | Kuo et al. | 514/54.2 |
| 5,358,973 | 10/1994 | Lindblad | 514/777 |
| 5,470,964 | 11/1995 | Qin | 536/20 |
| 5,478,477 | 12/1995 | Ramesh et al. | 210/728 |
| 5,534,589 | 7/1996 | Hager et al. | 524/801 |
| 5,562,924 | 10/1996 | Perrier | 424/499 |

FOREIGN PATENT DOCUMENTS

| | | |
|---|---|---|
| 0341745 A1 | 5/1989 | European Pat. Off. . |
| 0427316 A2 | 10/1990 | European Pat. Off. . |
| 0464727 A2 | 6/1991 | European Pat. Off. . |
| 0 507 604 A2 | 10/1992 | European Pat. Off. . |
| 54-036388 | 3/1979 | Japan . |
| 58-089397 | 8/1983 | Japan . |
| 01190614 | 7/1989 | Japan . |

OTHER PUBLICATIONS

Merck Manual of Diagnosis and Therapy—10th Ed., 1992, pp. 1338–1342.
Balazs et al., J. Equine Vet. Sci., 5, pp. 217–228 (1985).
Weiss et al., Semin. Arthritis Rheum., 11, p. 143 (1981).
Nakimi et al., Int. J. Clin. Pharmcol., Therapy Toxicology, 20, p. 501 (1982).
Grecomoro et al., Pharmatherapeutica, 5, p. 137 (1987).
Briganiti et al., Clinical Trials J., 24, p. 333 (1987).
Dahlberg et al., Arthritis & Rheumatism, 37, p. 521 (1994).
Brown et al., Exp. Physiol., 76, p. 125 (1991).
Bollet, J. Biol. Chem., 238, p. 3522 (1963).
Wong et al., J. Inorg. Biochem., 14, p. 127 (1981).
Miller et al., J. Bone & Joint Surgery, 40, p. 636 (1958).

*Primary Examiner*—Edward J. Webman
*Attorney, Agent, or Firm*—Martin F. Sloan; Mark Goldberg

[57] ABSTRACT

Acidic polysaccharides crosslinked by reaction with di- or polyanhydrides. The use of anhydride-crosslinked hyaluronic acid as a treatment for arthritis, as a drug delivery vehicle, to reduce the incidence of post-operative adhesion formation, to promote the healing of chronic wounds and ulcers, and as a component of cosmetic formulations.

4 Claims, No Drawings

ACIDIC POLYSACCHARIDES CROSSLINKED WITH POLYCARBOXYLIC ACIDS AND THEIR USES

FIELD OF THE INVENTION

This invention relates to acidic polysaccharides crosslinked by reaction with di- or polyanhydrides, and preferably hyaluronic acid crosslinked with dianhydrides. The crosslinked hyaluronic acid may be used as a treatment for arthritis, as a drug delivery vehicle, to reduce the incidence of post-operative adhesion formation, to promote the healing of chronic wounds and ulcers, and as a component of cosmetic formulations.

BACKGROUND OF THE INVENTION

The synovial fluid found in mammalian joints functions as a lubricant and shock absorber. The most important component of the synovial fluid is sodium hyaluronate, which makes the greatest contribution to the mechanical properties of the fluid. Hyaluronic acid is a naturally occurring high molecular weight glycosaminoglycan having a repeating disaccharide unit of D-glucuronic acid and N-acetylglucosamino-2-acetamido-2-desoxy-D-glucose joined by a $\beta 1 \rightarrow 3$ glucosidic bond. The disaccharides are joined to form an unbranched, uncrosslinked polysaccharide chain by $\beta 1 \rightarrow 4$ glucosidic bonds. In addition to its presence in synovial fluids, hyaluronic acid occurs in cell coats, pericellular gels, the extracellular matrix substance of connective tissues of vertebrates, the vitreous humor of the eye, human umbilical cord tissue, rooster combs and in some bacteria.

In healthy synovial fluid, the molecular weight of the sodium hyaluronate is very high, ranging from 1,600,000 to 10,900,000. Because the molecular weight is so high, even dilute solutions exhibit significant viscoelastic properties. In typical human synovial fluid the concentration of sodium hyaluronate is about 0.3%.

During inflammation of a joint caused by osteo- or rheumatoid arthritis both the molecular weight of hyaluronic acid and its concentration are reduced. This lowering of molecular weight decreases the ability of synovial fluid to act as a shock absorber, and thus the fluid does not provide adequate protection for the cartilage of the joint. In the case of advanced arthritis the cartilage is corroded away, leading to pain when the joint is in motion (see for example, "The Merck Manual of Diagnosis and Therapy-16th Edition", p 1338-42).

Relatively moderate molecular weight sodium hyaluronate has been used successfully as a supplemental synovial fluid in the leg joint of race horses (Balazs et al., J. Equine Vet. Sci., p. 217-228, 1985). However human synovial fluid contains substantially higher molecular weight sodium hyaluronate than that of horses.

Solutions of sodium hyaluronate also have been tested as supplemental synovial fluid for human osteoarthritic joints by injection into the joints. Treatment of arthritis by injection of sodium hyaluronate has been disclosed by Weiss et al., Semin. Arthritis Rheum., 11, p. 143, (1981); Nakimi et al., J. Clin. Pharmcol. Therapy Toxicology, 20, p. 501, (1982); Grecomoro et al., Pharmatherapeutica, 5, p. 137, (1987) and Briganiti et al., Clinical Trials Journal, 24, p. 333, (1987). However, the most recent evaluations of such procedures indicate that intra-articular injections of sodium hyaluronate solutions do not perform measurably differently from placebos (Dahlberg et al., in "Arthritis & Rheumatism" 37, p.521, 1994). Brown et al. in Exp. Physiol. 76, p.125, (1991), showed that the half-life of hyaluronic acid injected in a joint is only about 13 hours. Dahlberg, vide supra, has pointed out that a 13 hour half-life is short for therapeutic value.

One of the causes for the high rate of loss of sodium hyaluronate from the synovial cavity is the degradation of the molecule by enzymes and hydroxy radicals. Enzymes such as hyaluronidase, glucuronidase and glucosidase are found in the human body (A. J. Bollet, J. Biological Chem., 238, p. 3522, 1963). The most active enzyme is hyaluronidase, which cuts sodium hyaluronate along the backbone. The other two enzymes attack the polymer from the ends.

Hydroxy radicals come from two sources. The primary source is white blood cells, where macrophages and neutrophils release xanthine peroxidase and other enzymes to form superoxide anion, hydrogen peroxide and hypochlorite, which upon breakdown form hydroxy radical. Another source for hydroxy radical is the reduction of oxygen by reducing agents in the presence of iron. A common reducing agent in the body is ascorbic acid. Oxygen is reduced by iron(II) to form superoxide anion, which then reacts with iron (III) to form hydrogen peroxide. Hydrogen peroxide is reduced to hydroxy radical.

Increasing the molecular weight of sodium hyaluronate by crosslinking has been accomplished in a number of ways. Sakurai et al. in U.S. Pat. No. 4,716,224, disclose crosslinked hyaluronic acid or salts thereof prepared by crosslinking hyaluronic acid or its salts with a polyfunctional epoxide. The crosslinked compositions are stated to be resistant to hyaluronidase enzyme and possibly to be useful in treatment of arthritis and as a component of cosmetics. In U.S. Pat. No. 4,863,907 Sakurai et al. disclose crosslinked glycosaminoglycan or salts thereof, prepared by crosslinking a glycosaminoglycan or a salt thereof with a polyfunctional epoxy compound. The crosslinked compositions are stated to have excellent resistance to glycosidase enzyme and to be useful in medical devices, ophthalmologic drugs and cosmetics.

Huang et al., in European Patent Application No. 0 507 604 A2, disclose ionically crosslinked carboxyl-containing polysaccharides where the crosslinking agent is a compound possessing a trivalent cation. The compositions are stated to be useful in preventing post-operative adhesion formation following surgery.

Mälson et al., in U.S. Pat. No. 4,716,154 disclose crosslinking hyaluronic acid with bi- or polyfunctional epoxides or their corresponding halohydrins, epihalohydrins or halides, and divinyl sulfone. The crosslinked materials are said to be useful as substitutes for vitreous humor of the eye. Mälson et al., in U.S. Pat. No. 4,772,419 also disclose crosslinking hyaluronic acid with polyfunctional epoxides.

In U.S. Pat. No. 4,957,744 della Valle et al. disclose crosslinked esters of hyaluronic acid prepared by esterifying the carboxyl groups of hyaluronic acid with polyhydric alcohols. It is proposed that the crosslinked materials be used as therapeutic agents, e.g. as drugs for treatment of arthritis, and as ingredients of cosmetic formulations.

Balazs et al., in U.S. Pat. Nos. 4,582,865, 4,605,691 and 4,636,524, disclose crosslinking of hyaluronic acid and its salts, and of other polysaccharides, by reaction with divinylsulfone. In U.S. Pat. Nos. 5,128,326 and 4,582,865, Balazs et al. disclose crosslinking hyaluronic acid with formaldehyde, epoxides, polyaziridyl compounds and divinyl sulfone. In U.S. Pat. No. 4,713,448 Balazs et al. disclose chemically modifying hyaluronic acid by reaction with aldehydes such as formaldehyde, glutaraldehyde and glyoxal, and teach the possibility that crosslinking has occurred. In U.S. Pat. Nos. 4,582,865, 4,605,691, 4,636,524, 5,128,326, 4,582,865 and 4,713,448 the uses disclosed for the products are cosmetic formulations and drug delivery systems.

In U.S. Pat. No. 5,356,883 Kuo et al. disclose crosslinking hyaluronic acid by reaction with biscarbodiimides. The hydrogels that are produced are taught to have utility as biocompatible gel, films or sponges.

SUMMARY OF THE INVENTION

This invention pertains to crosslinked compositions comprising linked polysaccharides containing acidic groups or their salts, wherein at least one hydroxyl group of each linked polysaccharide is esterified with a carboxyl group contained in a polycarboxylic acid containing at least four carboxyl groups, and at least two carboxyl groups of the polycarboxylic acid are esterified with hydroxyl groups of the polysaccharides. A novel feature of the crosslinked compositions is the ester linkage formed from hydroxyl groups on the polysaccharide and the tetracarboxylic acid.

In a preferred embodiment the polysaccharide comprises hyaluronic acid or a salt of hyaluronic acid; the polycarboxylic acid is a tetracarboxylic acid, and the crosslinked composition has substantially greater resistance to the enzyme hyaluronidase and to hydroxy radicals than hyaluronic acid or its sodium salt.

In another embodiment the invention pertains to a method for crosslinking a polysaccharide containing acidic groups which comprises reacting the polysaccharide with a di- or polyanhydride.

In another embodiment the invention also pertains to pharmaceutical compositions for treating mammalian arthritis, for preventing post-operative adhesion formation and for promoting the healing of chronic wounds, comprising as the active component the crosslinked hyaluronic acid of this invention, or its pharmaceutically acceptable salts.

In a further embodiment the invention pertains to drug delivery systems and cosmetic compositions comprising the crosslinked hyaluronic acid of this invention.

In yet another embodiment the invention pertains to methods for treating mammalian arthritis, reducing the incidence of post-operative adhesion formation and promoting the healing of chronic wounds and ulcers comprising injecting or applying an effective amount of a pharmaceutical composition comprising as the active component the crosslinked hyaluronic acid of this invention, or its pharmaceutically acceptable salts.

DETAILED DESCRIPTION OF THE INVENTION

The crosslinked compositions of this invention comprise linked polysaccharides containing acidic groups or their salts, wherein at least one hydroxyl group of each linked polysaccharide is esterified with a carboxyl group contained in a polycarboxylic acid containing at least four carboxyl groups, and at least two carboxyl groups of the polycarboxylic acid are esterified with hydroxyl groups of the polysaccharides.

The preferred acidic groups comprise at least one member selected from the group consisting of carboxyl, sulfate, sulfite and phosphate. The most preferred acidic group is the carboxyl group.

Preferred polysaccharides for use in this invention comprise those selected from the group consisting of hyaluronic acid, chondroitin sulfate, keratan sulfate, dermatan sulfate, heparan sulfate, heparin, carboxymethyl cellulose, pectin, alginic acid, polygalacturonic acid, polymannuronic acid, polyglucuronic acid and carrageenan. The most preferred is hyaluronic acid.

The preferred salts in the operation of this invention comprise salts of an alkali or alkaline earth metal, aluminum or ammonium. The most preferred salt is a salt of sodium.

The preferred polycarboxylic acids of this invention are tetracarboxylic acids, which comprise members selected from the group consisting of:

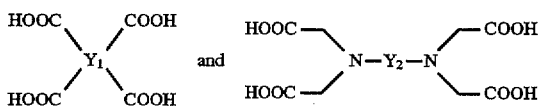

where $Y_1$ is a tetravalent organic radical selected from the group consisting of aliphatic, aromatic, cycloaliphatic, heterocyclic and polymeric radicals, and where $Y_2$ is a divalent organic radical selected from the group consisting of aliphatic, aromatic, cycloaliphatic, heterocyclic and polymeric radicals.

Preferably $Y_1$ is selected from the group consisting of 1,2,3,4-tetrasubstituted benzene, 1,2,4,5-tetrasubstituted benzene, 1,2,5,6-tetrasubstituted naphthalene, 1,2,4,5-tetrasubstituted naphthalene, 1,2,6,7-tetrasubstituted naphthalene, 1,2,7,8-tetrasubstituted naphthalene, 2,3,6,7-tetrasubstituted naphthalene, 1,4,5,8-tetrasubstituted naphthalene, 2,3,2',3'-tetrasubstituted biphenyl, 3,4,2',3'-tetrasubstituted biphenyl, 3,4,3',4'-tetrasubstituted biphenyl, 1,2,3,4-tetrasubstituted anthracene, 1,2,5,6-tetrasubstituted anthracene, 1,2,6,7-tetrasubstituted anthracene, 1,2,7,8-tetrasubstituted anthracene, 2,3,6,7-tetrasubstituted anthracene, 1,2,3,4-tetrasubstituted phenanthrene, 1,2,7,8-tetrasubstituted phenanthrene, 1,2,6,7-tetrasubstituted phenanthrene, 1,2,5,6-tetrasubstituted phenanthrene, 2,3,6,7-tetrasubstituted phenanthrene, 1,8,9,10-tetrasubstituted phenanthrene, 3,4,9,10-tetrasubstituted perylene, 2,3,5,6-tetrasubstituted pyrazine, 2,3,4,5-tetrasubstituted thiophene, 2,3,4,5-tetrasubstituted pyrrolidine,

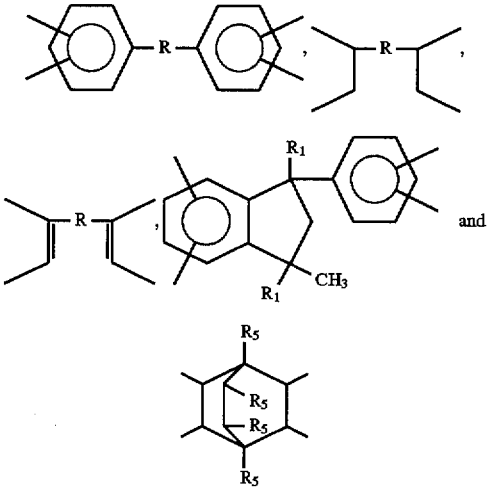

where R comprises linear, branched, or cyclic alkyl, aryl, —O—, —S—, —SO$_2$—, —CO—, —COO—, —NR$_1$—, —CONR$_1$—, —COS—, —N=N—, —N(O)=N—, —CR$_2$R$_3$—, —CH$_2$—, —CHR$_2$—, —R$_4$—, —SiR$_2$R$_3$—, —OSiR$_2$R$_3$O—, —POR$_2$—, —POR$_2$O— and —A—X—B—;

where $R_1$ is hydrogen or $C_1$–$C_5$ alkyl;

where $R_2$, $R_3$ and $R_4$, which can be the same or different, are linear or cyclic alkyl, aryl, substituted aryl, perfluoroalkyl and perfluoroaryl;

where $R_5$ is hydrogen, alkyl, aryl, or aralkyl;

where A and B, which can be the same or different, are —O—, —S—, —CO—, —SO$_2$—, —SO—, —POR$_2$—, —POR$_2$O—, —SiR$_2$R$_3$—, —CONHR$_2$—, —CONH—, —NR$_1$— and —NH—; and where X is an oligomer of a polyalkylene ether, polyalkylene thioether, polyaryl ether, polyester, polybutadiene, polyarylether sulfone, polyetherimide, polyamide, polyamic acid, polyamide imide, polyimide, polyalkyl phenol, polyphenol, polyamine, polysiloxane, polyvinyl alcohol, polyurethane, polyurea and polycarbonate.

$Y_2$ is preferably selected from the group consisting of polyethers, polythioethers, polyesters, polyamides, polyimides, polyamic acids, polyamide imides, polysulfones, polyhydantoins, polyamines, polyurethanes, polyureas, polysiloxanes, tetracarbonates and polybutadiene.

Exemplary tetracarboxylic acids are 3,4,3',4'-benzophenone tetracarboxylic acid, 2,3,6,7-naphthalene tetracarboxylic acid, 1,4,5,8-naphthalene tetracarboxylic acid, 1,2,4,5-naphthalene tetracarboxylic acid, 1,2,5,6-naphthalene tetracarboxylic acid, 3,4,3'4'-diphenyl tetracarboxylic acid, 2,3,2',3'-diphenyl tetracarboxylic acid, 2,2-bis(3,4-dicarboxyphenyl)propane, 3,4,9,10-perylene tetracarboxylic acid, bis(3,4-dicarboxyphenyl)ether, 1,1-bis(2,3-dicarboxyphenyl)ethane, bis(3,4-dicarboxyphenyl) methane, decahydronaphthalene-1,4,5,8-tetracarboxylic acid, 4,8-dimethyl-1,2,3,4,5,6,7-hexahydronaphthalene-1,2,5,6-tetracarboxylic acid, pyromellitic acid, 2,6-dichloronaphthalene-1,4,5,8-tetracarboxylic acid, cyclopentane tetracarboxylic acid, pyrrolidine-2,3,4,5-tetracarboxylic acid, pyrazine-2,3,5,6-tetracarboxylic acid, thiophene-2,3,4,5-tetracarboxylic acid, ethylenediamine tetraacetic acid, diethylenetriamine pentaacetic acid, 4,4-sulfonyldiphthalic acid and 1-(3,4-dicarboxyphenyl)-1,3,3-trimethylindane-5,6(6,7)-dicarboxylic acid, 2,2'-bis(2,3-dicarboxyphenyl)propane, 1,1'-bis(3,4-dicarboxyphenyl) ethane, 1-(3'4-dicarboxyphenyl)-3-methylindane-5,6(6,7)-dicarboxylic acid, 3,4-dicarboxy-1,2,3,4-tetrahydro-1-naphthalenesuccinic acid, 1-methyl-3,4-dicarboxy-1,2,3,4-tetrahydro-1-naphthalenesuccinic acid, 3,4,9,10-perylene tetracarboxylic acid, 1,8,9,10-phenanthrene tetracarboxylic acid, 2,6-dichloronaphthalene-1,4,5,8-tetracarboxylic acid, 2,7-dichloronaphthalene-1,4,5,8-tetracarboxylic acid, 2,3,6,7-tetrachloronaphthalene-1,4,5,8-tetracarboxylic acid, 2,3,3',4'-benzophenone tetracarboxylic acid, 2,3,2',3'-benzophenone tetracarboxylic acid, 4,4'-oxodiphthalic acid, 3,3'-oxodiphthalic acid, 4,4'-thiodiphthalic acid, 3,3'-thiodiphthalic acid and 2,3,5,6-bicyclo(2,2,2)octane tetracarboxylic acid.

The most preferred tetracarboxylic acids are pyromellitic acid and 3,4,3',4'-benzophenone tetracarboxylic acid.

Operable polycarboxylic acids having more than four carboxyl groups comprise members selected from the group consisting of styrene/maleic acid copolymers, alkyl vinyl ether/maleic acid copolymers and:

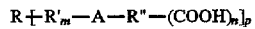

where n is 2 or 3, m is 0 or 1, p is 2 to about 100,000, R is aryl or saturated or unsaturated $C_1$–$C_{100,000}$ alkyl, R' is aryl or saturated or unsaturated $C_1$–$C_{10}$ alkyl, R" is aryl or saturated or unsaturated $C_2$–$C_{30}$ alkyl and A is:

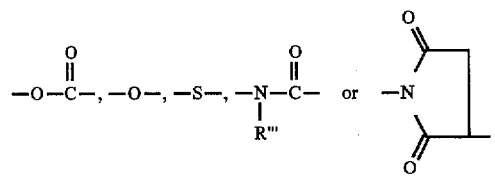

where R'" is aryl or saturated or unsaturated $C_1$–$C_{10}$ alkyl.

It has been found that when the crosslinked composition is derived from hyaluronic acid or its salts, the crosslinked composition has substantially greater resistance to degradation caused by hydroxy radical or enzymes, in particular hyaluronidase, than does hyaluronic acid itself or its salts.

For example, when an aqueous solution of sodium hyaluronate was treated with the enzyme hyaluronidase, the time it took to reduce the viscosity to one-half of the viscosity measured at 10 minutes (the viscosity half-life) was only 0.5 hours. However, when the test was carried out under the same conditions on a crosslinked composition of this invention where the polysaccharide was hyaluronic acid and the tetracarboxylic acid was pyromellitic acid or 3,4,3',4'-benzophenone tetracarboxylic acid, the viscosity half-life was 34 hours or 30 hours respectively.

In the tests for degradation by hydroxy radical the hydroxy radicals were generated by reaction of ferric chloride with ascorbic acid as described by Wong et al. Inorganic Biochemistry, 14, p. 127 (1981), which publication is incorporated herein in its entirety by reference. In a typical test the viscosity half-life was 0.9 hours for hyaluronic acid. When the same test was carried out under the same conditions on a crosslinked composition of this invention wherein the polysaccharide was hyaluronic acid and the tetracarboxylic acid was pyromellitic acid or 3,4,3',4'-benzophenone tetracarboxylic acid, the viscosity half-life was 24 hours or 6 hours respectively.

In another embodiment, the invention pertains to a method for crosslinking the acidic polysaccharides or their salts, comprising reacting the polysaccharides with a di- or polyanhydride, where polyanhydrides are defined to mean those anydrides containing more than two anhydride groups per molecule.

The dianhydrides operable in the method of this invention comprise members of the group selected from:

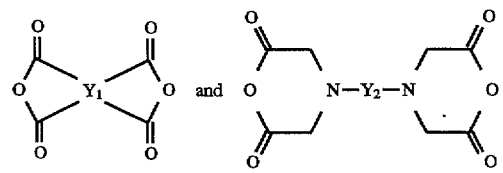

where $Y_1$ is a tetravalent organic radical selected from the group consisting of aliphatic, aromatic, cycloaliphatic, heterocyclic and polymeric radicals, and where $Y_2$ is a divalent organic radical selected from the group consisting of aliphatic, aromatic, cycloaliphatic, heterocyclic and polymeric radicals.

Preferably $Y_1$ is selected from the group consisting of 1,2,3,4-tetrasubstituted benzene, 1,2,4,5-tetrasubstituted benzene, 1,2,5,6-tetrasubstituted naphthalene, 1,2,4,5-tetrasubstituted naphthalene, 1,2,6,7-tetrasubstituted naphthalene, 1,2,7,8-tetrasubstituted naphthalene, 2,3,6,7-tetrasubstituted naphthalene, 1,4,5,8-tetrasubstituted naphthalene, 2,3,2',3'-tetrasubstituted biphenyl, 3,4,2',3'-tetrasubstituted biphenyl, 3,4,3',4'-tetrasubstituted biphenyl, 1,2,3,4-tetrasubstituted anthracene, 1,2,5,6-tetrasubstituted anthracene, 1,2,6,7-tetrasubstituted anthracene, 1,2,7,8-tetrasubstituted anthracene, 2,3,6,7-tetrasubstituted anthracene, 1,2,3,4-tetrasubstituted phenanthrene, 1,2,7,8-tetrasubstituted phenanthrene, 1,2,6,7-tetrasubstituted phenanthrene, 1,2,5,6-tetrasubstituted phenanthrene, 2,3,6,7-tetrasubstituted phenanthrene, 1,8,9,10-tetrasubstituted phenanthrene, 3,4,9,10-tetrasubstituted perylene, 2,3,5,6-tetrasubstituted pyrazine, 2,3,4,5-tetrasubstituted thiophene, 2,3,4,5-tetrasubstituted pyrrolidine,

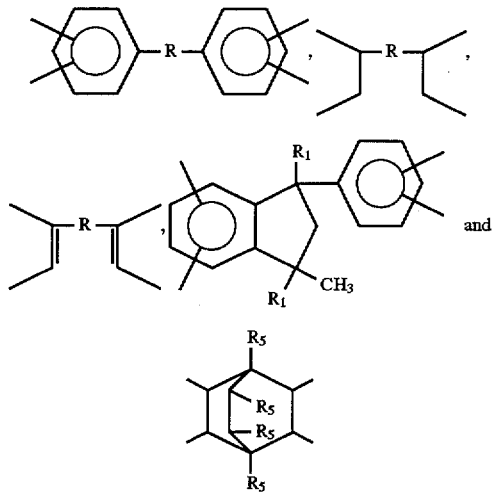

where R comprises linear, branched, or cyclic alkyl, aryl, —O—, —S—, —SO$_2$—, —CO—, —COO—, —NR$_1$—, —CONR$_1$—, —COS—, —N=N—, —N(O)=N—, —CR$_2$R$_3$—, —CH$_2$—, —CHR$_2$—, —R$_4$—, —SiR$_2$R$_3$—, —OSiR$_2$R$_3$O—, —POR$_2$—, —POR$_2$O— and —A—X—B—;

where R$_1$ is hydrogen or C$_1$–C$_5$ alkyl;

where R$_2$, R$_3$ and R$_4$, which can be the same or different, are linear or cyclic alkyl, aryl, substituted aryl, perfluoroalkyl and perfluoroaryl;

where R$_5$ hydrogen, alkyl, aryl, or aralkyl;

where A and B, which can be the same or different, are —O—, —S—, —CO—, —SO$_2$—, —SO—, —POR$_2$—, —POR$_2$O—, —SiR$_2$R$_3$—, —CONHR$_2$—, —CONH—, —NR$_1$— and —NH—; and where X is an oligomer of a polyalkylene ether, polyalkylene thioether, polyaryl ether, polyester, polybutadiene, polyarylether sulfone, polyetherimide, polyamide, polyamic acid, polyamide imide, polyimide, polyalkyl phenol, polyphenol, polyamine, polysiloxane, polyvinyl alcohol, polyurethane, polyurea and polycarbonate.

Y$_2$ is preferably selected from the group consisting of polyethers, polythioethers, polyesters, polyamides, polyimides, polyamic acids, polyamide imides, polysulfones, polyhydantoins, polyamines, polyurethanes, polyureas, polysiloxanes, tetracarbonates and polybutadiene.

The dianhydrides are preferably selected from the group consisting of 3,4,3',4'-benzophenone tetracarboxylic acid dianhydride, 2,3,6,7-naphthalene tetracarboxylic acid dianhydride, 1,4,5,8-naphthalene tetracarboxylic acid dianhydride, 1,2,4,5-naphthalene tetracarboxylic acid dianhydride, 1,2,5,6-naphthalene tetracarboxylic acid dianhydride, 3,4,3',4'-diphenyl tetracarboxylic acid dianhydride, 2,3,2',3'-diphenyl tetracarboxylic acid dianhydride, 2,2-bis(3,4-dicarboxyphenyl)propane dianhydride, 3,4,9,10-perylene tetracarboxylic acid dianhydride, bis(3,4-dicarboxyphenyl)ether dianhydride, 1,1-bis(2,3-dicarboxyphenyl)ethane dianhydride, bis(3,4-dicarboxyphenyl)methane dianhydride, decahydronaphthalene-1,4,5,8-tetracarboxylic acid dianhydride, 4,8-dimethyl-1,2,3,4,5,6,7-hexahydronaphthalene-1,2,5,6-tetracarboxylic acid dianhydride, pyromellitic acid dianhydride, 2,6-dichloronaphthalene-1,4,5,8-tetracarboxylic acid dianhydride, cyclopentane tetracarboxylic acid dianhydride, pyrrolidine-2,3,4,5-tetracarboxylic acid dianhydride, pyrazine-2,3,5,6-tetracarboxylic acid dianhydride, thiophene-2,3,4,5-tetracarboxylic acid dianhydride, ethylenediamine tetraacetic acid dianhydride, diethylenetriamine pentaacetic acid dianhydride, 4,4-sulfonyldiphthalic acid dianhydride, 2,2'-bis(2,3-dicarboxyphenyl)propane dianhydride, 1-(3,4-dicarboxyphenyl)-1,3,3-trimethylindane-5,6(6,7)-dicarboxylic acid dianhydride, 1,1'-bis(3,4-dicarboxyphenyl)ethane dianhydride, 1-(3'4-dicarboxyphenyl)-3-methylindane-5,6(6,7)-dicarboxylic acid dianhydride, 3,4-dicarboxy-1,2,3,4-tetrahydro-1-naphthalenesuccinic acid dianhydride, 1-methyl-3,4-dicarboxy-1,2,3,4-tetrahydro-1-naphthalenesuccinic acid dianhydride, 3,4,9,10-perylene tetracarboxylic acid dianhydride, 1,8,9,10-phenanthrene tetracarboxylic acid dianhydride, 2,6-dichloronaphthalene-1,4,5,8-tetracarboxylic acid dianhydride, 2,7-dichloronaphthalene-1,4,5,8-tetracarboxylic acid dianhydride, 2,3,6,7-tetrachloronaphthalene-1,4,5,8-tetracarboxylic acid dianhydride, 2,3,3',4'-benzophenone tetracarboxylic acid, 2,3,2',3'-benzophenone tetracarboxylic acid dianhydride, 4,4'-oxodiphthalic acid dianhydride, 3,3'-oxodiphthalic acid dianhydride, 4,4'-thiodiphthalic acid dianhydride, 3,3'-thiodiphthalic acid dianhydride and 2,3,5,6-bicyclo(2,2,2) octane tetracarboxylic acid dianhydride.

The most preferred dianhydrides are pyromellitic acid dianhydride and 3,4,3',4'-benzophenone tetracarboxylic acid dianhydride.

Polyanhydrides operable in carrying out the method of this invention are members selected from the group consisting of styrene/maleic anhydride copolymers, alkyl vinyl ether/maleic anhydride copolymers and:

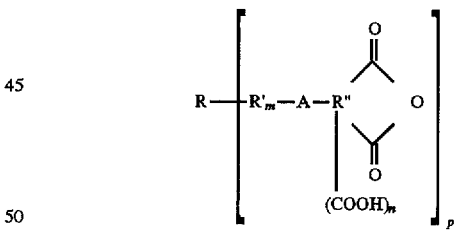

where where n is 0 or 1, m is 0 or 1, p is 2 to about 100,000, R is aryl or saturated or unsaturated C$_1$–C$_{100,000}$ alkyl, R' is aryl or saturated or unsaturated C$_1$–C$_{10}$ alkyl, R" is aryl or saturated or unsaturated C$_2$–C$_{30}$ alkyl and A is:

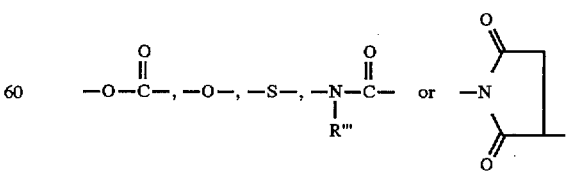

where R''' is aryl or saturated or unsaturated C$_1$–C$_{10}$ alkyl. The most preferred polyanhydrides are obtained by reacting monomeric or polymeric polyols or polyamines with an excess of dianhydride, wherein the number of equivalents of anhydride is at least twice that of the number of equivalents of hydroxyl or amine contained in the polyol or polyamine, or by reacting monomeric or polymeric polyols or polyamines with an excess of monoanhydride also containing an acyl halide, wherein the number of equivalents of anhydride plus acyl halide is at least twice that of the number of equivalents of hydroxyl or amine contained in the polyol or polyamine.

Because anhydride functionality is readily hydrolyzable in water, it is preferred that the reaction of the di- or polyanhydrides with polysaccharide be carried out in a polar, aprotic solvent. Preferred solvents are N-methyl pyrrolidinone, N-ethyl pyrrolidinone, N-cyclohexyl pyrrolidinone, 4-methyl morpholine N-oxide, dimethyl formamide, sulfolane and dimethyl sulfoxide.

Salts of the acidic polysaccharides may not be soluble in the preferred solvents. In particular, the sodium salt of hyaluronic acid is not soluble in the preferred solvents, and so it is generally convenient for the purpose of this embodiment to convert the sodium salt to a tetraalkyl ammonium salt to increase solubility. After the crosslinking reaction of the tetraalkyl ammonium salt and the dianhydride, the product can then be converted back to the sodium form by ion exchange.

In the crosslinking reaction the ratio of di- or polyanhydride to polysaccharide is most readily expressed in terms of the equivalents of anhydride contained in the di-or polyanhydride per equivalent of repeating unit in the polysaccharide. For the purpose of the invention the ratio is from about 0.05 to about 4 equivalents of anhydride per equivalent of repeating unit. A preferred ratio is from about 0.08 to about 2, and the most preferred ratio from about 0.4 to about 1.6.

In still other embodiments the invention pertains to pharmaceutical compositions for treating mammalian arthritis, for preventing post-operative adhesions and for promoting the healing of chronic wounds and ulcers. The active component of these pharmaceutical compositions comprises crosslinked hyaluronic acid, or a pharmaceutically acceptable salt of crosslinked hyaluronic acid, wherein at least one hydroxyl group of each linked hyaluronic acid is esterified with a carboxyl group contained in a polycarboxylic acid containing at least four carboxyl groups, and at least two carboxyl groups of the polycarboxylic acid are esterified with hydroxyl groups of the hyaluronic acid.

Pharmaceutically acceptable salts are preferably salts of an alkali or alkaline earth metal, aluminum or ammonium. The most preferred pharmaceutically acceptable salt is sodium.

The methods and compositions of this invention can be used to prevent post-operative adhesions in any animal that is susceptible to unwanted adhesion formation following surgery. The method and compositions are used to prevent adhesions from developing in mammals, preferably human beings. They are useful in all types of surgery where it is desired to inhibit the formation of post-surgical adhesions, e.g., abdominal surgery, gynecological surgery, thoracic surgery, orthopedic surgery, neurological surgery and ophthalmological surgery.

The adhesion preventative may be administered to the site of surgical trauma by any convenient mode such as, for example, by lavage, by coating directly on the site in a gel, cream, film or foam, or by any other convenient method. The administration of the adhesion preventative can occur at any time before significant wound healing has occurred. It is preferred to administer it at the conclusion of surgery, just prior to closing of the wound. However, in some cases it may be desirable to administer the preventative continually over a period of time. An effective amount of adhesion preventative is an amount necessary to affect a reduction in the incidence of post-operative surgical adhesions. Preferably, the amount should be enough to coat the entire area exposed to the surgical trauma, and if desired an additional amount sufficient to coat body tissue adjacent to the area of trauma. The effective amount can be readily determined empirically.

The compositions of this invention can also be used to promote the healing of chronic wounds, e.g. burns, and ulcers, e.g. diabetes foot ulcers in mammals, in particular, human beings. Hyaluronic acid retains moisture and also has angiogenesis characteristics that make it useful for this application. When utilized for wound healing the compositions may be used alone in aqueous solution, preferably physiological saline solution, or the solutions may be combined with wound healing drugs and other water soluble polymers. They may be administered to the site of the wound or ulcer by any convenient mode such as, for example, by lavage, by coating directly on the site in a gel, cream, film or foam, by impregnation in a bandage or wound dressing that is applied to wound or ulcer, or by any other convenient method. An effective amount to promote healing is enough to coat the entire area of the wound or ulcer and if desired an additional amount sufficient to coat body tissue adjacent to the wound or ulcer. The effective amount can be readily determined empirically. A typical anhydride-crosslinked hyaluronic acid may contain as other ingredients water-soluble polymers, antibiotics, immunosuppressants and pain reducers.

In the application of the crosslinked hyaluronic acid of this invention to the treatment of arthritis in mammals, in particular human beings, the crosslinked hyaluronic acid is usually dissolved in physiological saline to a sufficient viscosity to pass through an injection needle, not more than about 50,000 cps, preferably about 5,000 to about 30,000 cps. The treatment solution is then injected into the diseased joint.

A typical knee joint synovial fluid supplementation injection procedure is similar to one described by Miller et al. in J. Bone and Joint Surgery, 40, p.636 (1985), which publication is incorporated herein by reference. A sterile solution, 2.5 ml, of the sodium salt of anhydride-crosslinked hyaluronic acid (concentration of crosslinked hyaluronic acid 10 mg/ml) in buffered saline (sodium chloride 8.5 mg/ml, dibasic sodium phosphate 0.537 mg/ml, sodium dihydrogen phosphate 0.016 mg/ml) is slowly drawn into a syringe to ensure the absence of air pockets. The knee is then prepared for injection by cleaning with soap, wiping with cetyl trimethylammonium bromide and painting with tincture of iodine. The solution is injected into a synovium cavity through a premarked triangular arc at the lateral side of the joint bound by the tibial plateau, the edge of the ligamentum patellae, and the curve of the lateral femoral condyle. Local anaesthesia may be used prior to injection. In certain cases knee aspiration with the buffered saline solution may be needed prior to the synovial fluid supplementation injection. Such a procedure is described by Dahlberg et al. in Arthritis & Rheumatism, 37, 1994, page 521, which article is incorporated herein by reference.

The injectable solution may contain materials in addition to the crosslinked hyaluronic acid. These include water soluble polymers such as chondroitin sulfate, dermatan sulfate, and/or a phospholipid to improve the lubricity of the solution. Anesthetics, anti-inflammatory reagents, antibiotics, antibacterials, cytotoxins and sugars may be added also.

Anhydride-crosslinked hyaluronic acid may be used as a drug delivery system. The crosslinked hyaluronic acid forms a molecular cage in which molecules with pharmacological activity can be dispersed. The substances contained in the cage are delivered into the environment by diffusion. The drug molecule, or mixture of drug molecules, may be covalently or non-covalently bonded to the hyaluronic acid. The covalent bonding can be via attachment to the carboxylic acid or hydroxyl groups of the hyaluronic acid moieties. The gels, films, threads, particles or sponges of anhydride-crosslinked hyaluronic acid may be placed, sprayed, ingested, injected or implanted at the location where the contained pharmacological substance is needed. These substances may be therapeutic drugs (such as anesthetics, analgesics, anti-inflammatories, diuretics, antagonists, antibiotics, hormones, antirheumatics, adrenergic agonists, cytostatics, antihypertensives or immunosuppressant agents), growth factors, enzymes or cellular anti-adhesion compounds.

The crosslinked hyaluronic acid of this invention can also function as a component of cosmetics for topical uses. Because hyaluronic acid has been shown to hold moisture under low relative humidity conditions and yield a pleasant and smooth feeling at high relative humidities, it has been used as a moisturizer in cosmetic formulations. The crosslinked hyaluronic acid of this invention will provide similar effects. Mixtures of crosslinked hyaluronic acid with other low cost water-soluble polymers such as carboxymethyl cellulose, pectin, alginate, soy protein, casein and gelatin may also be employed.

Natural extracts of plant sources, such as cactus aloe vera, mesquite, matricaria chamomilla, tumeric, carrot, jojoba, rose and others, may be blended into a cosmetic formulation containing crosslinked hyaluronic acid. Alpha hydroxy acids such as lactic and hydroxy ethanoic may be added to the formulation to improve the plasticity of the skin.

A typical anti-aging cosmetic composition is: 2-hydroxyethanoic acid, 7%, propylene glycol, 15%, crosslinked hyaluronic acid solution (1 g/100 ml), 1%, water, 60% and ethyl alcohol, 17%, where all percentages are by weight.

A formulation for facial soft gel is: aqueous slurry of carboxymethyl cellulose (3 g/100 ml), 25%, aqueous solution of triethanolamine (10 g/100 ml), 11%, Methyl Gluceth-10, 5%, crosslinked hyaluronic acid aqueous solution (1 g/100 ml), 1%, perfume and preservatives, 1%, water, 57%, where all percentages are be weight.

A typical essential skin moisturizer composition is hydroxyethyl cellulose, 0.5%, Methyl Gluceth-10, 2%, glycerin, 2%, crosslinked hyaluronic acid aqueous solution (1 g/100 ml), 1%, water, 94%, preservatives and perfume, 0.5%, where all percentages are by weight.

The invention is illustrated by the following Examples, which are provided for the purpose of representation, and are not to be construed as limiting the scope of the invention. All parts and percentages in the examples are by weight unless otherwise specified.

EXAMPLE 1

The example describes the preparation of a methyltricaprylylammonium salt of hyaluronic acid.

To a solution of 10 g of sodium hyaluronate (fermentation product, Chisso Corporation, Chiba, Japan) in 1000 ml of water was added a solution of 50 g. of methyltricaprylylammonium chloride (Aliquat 336, Aldrich Chemical, Milwaukee, Wis.) in 50 ml of acetone. The mixture was stirred overnight, and then the rubbery precipitate was filtered, washed with water and acetone, and then dried in vacuo overnight. It was again soaked in 500 ml of acetone for 7 hours and dried in vacuo overnight to yield 46.9 g of rubbery material.

EXAMPLES 2-9

These examples describe crosslinking of the methyltricaprylylammonium salt of hyaluronic acid with dianhydrides.

The product of Example 1, 2.0 g (0.46 meq of repeating unit), was dissolved in 100 ml of N-methylpyrrolidinone. To this solution was added a dianhydride, and then the mixture was tumble-stirred for 16 hours. The dianhydrides utilized were ethylenediamine tetraacetic acid dianhydride (EDTAA), diethylenetriamine pentaacetic acid dianhydride (DETPAA), 3,4,3',4'-benzophenone tetracarboxylic acid dianhydride (BTDA) and 4,4'oxodiphthalic acid dianhydride (OPDA). Examples 2 and 3 are controls utilizing no anhydride.

The data in Table 1 show the gelation at the end of the 16 hour stirring period, demonstrating the crosslinking of the methyltricaprylylammonium salt of hyaluronic acid. The viscosities are Brookfield viscosities.

TABLE 1

| Example No. | Initial Viscosity (cps) | Anhydride | Anhydride Amount, g | Anhydride Amount, millimoles | Final Viscosity (cps) |
|---|---|---|---|---|---|
| 2 | 2375 | — | 0.00 | — | 1505 |
| 3 | 2300 | — | 0.00 | — | 1555 |
| 4 | 2365 | EDTAA | 0.10 | 0.39 | gelled |
| 5 | 2340 | EDTAA | 0.15 | 0.59 | gelled |
| 6 | 2345 | DETPAA | 0.10 | 0.28 | gelled |
| 7 | 2300 | DETPAA | 0.15 | 0.42 | gelled |
| 8 | 2100 | BTDA | 0.10 | 0.31 | gelled |
| 9 | 2165 | OPDA | 0.10 | 0.32 | gelled |

EXAMPLES 10-17

These examples describe conversion of the crosslinked methyltricaprylylammonium salts of hyaluronic acid prepared in Examples 4-9 to the corresponding sodium salts.

To the solutions of crosslinked methyltricaprylylammonium salts of hyaluronic acid (Examples 4-9) in N-methylpyrrolidinone at 10° C. was added a solution of 1 g of salt in 50 ml of water. The resulting mixtures were stirred for 10 minutes, and then 10 ml of acetone was added. After 20 minutes the resulting precipitates were filtered, washed with 50 ml of 4/1 acetone/water five times, washed three times with 30 ml potions of acetone and then dried in a vacuum oven until a constant weight was obtained. The resulting materials were redissolved in 100 ml of phosphate buffered saline water (pH=7.4), and then the viscosities of the resulting solutions were measured. The data are in Table 2.

The substantial increase in viscosity found in Examples 12 and 16 and formation of substantial amounts of gel in Examples 13-15 and 17 indicate the crosslinked nature of the material.

TABLE 2

| Example No. | Crosslinked Salt | Sodium Salt, Viscosity of 0.4% Aq. Solution (cps) |
|---|---|---|
| 10 | Control, no crosslinking | 25 |
| 11 | Control, no crosslinking | 26 |
| 12 | Example 4 | 640 |
| 13 | Example 5 | 59 + insoluble gels |
| 14 | Example 6 | 22 + insoluble gels |
| 15 | Example 7 | 26 + insoluble gels |
| 16 | Example 8 | 199 |
| 17 | Example 9 | 11 + insoluble gels |

EXAMPLE 18

This example illustrates the resistance of the anhydride-crosslinked hyaluronic acid to degradation by hyaluronidase.

Samples of hyaluronic acid crosslinked by reaction with pyromellitic acid dianhydride (PMDA) or a mixture of PMDA and BTDA (1/1 by weight) were prepared by the methods of Examples 1–17. They were tested and evaluated according to the following procedure.

To a 100 ml aqueous solution of sodium salt of crosslinked hyaluronate (0.4% wt/vol, buffered at pH 7.4) was added 1 ml of a solution of hyaluronidase (EC 3.2.1.35; type I-S, from bovine testes, lyophilized, 290 units/mg, Sigma Chemical, St. Louis, Mo.) with the concentration of 290 units/ml was added. The mixture was shaken for about 10 seconds, and then the first viscosity (Brookfield) was measured after 10 minutes. The viscosity was then monitored for a period of time. The viscosity at 10 minutes was considered to be 100%. The degradation resistance of the sample was assessed by measuring the time required to reduce the viscosity to 50% of the 10 minute value (viscosity half-life). The control (Example 18A) consisted of sodium hyaluronate. The results are in Table 3.

TABLE 3

Hyaluronidase Test of Anhydride-crosslinked Hyaluronic Acid

| Example Number | Dianhydride | Viscosity Half-Life |
|---|---|---|
| 18A | — | 0.5 hours |
| 18B | BTDA | 30 |
| 18C | BTDA/PMDA | 34 |

EXAMPLE 19

This example illustrates the resistance of the anhydride-crosslinked hyaluronic acid to degradation by hydroxy radicals as generated by the reaction of ascorbic acid with ferric chloride.

Samples of hyaluronic acid crosslinked with PMDA and BTDA were prepared by the methods of Examples 1–17. They were tested and evaluated according to the following procedure.

To a 100 ml aqueous solution of sodium salt of crosslinked hyaluronate (0.4% wt/vol, buffered at pH 7.4) 1 ml of a 0.34M ferric chloride solution and 1 ml of 0.18M ascorbic acid solution were added. The mixture was shaken for about 10 seconds, and then the first viscosity (Brookfield) was measured after 10 minutes. The viscosity at this point was considered to be 100%. The degradation resistance of the sample was assessed by measuring the time required to reduce the viscosity to 50% of the 10 minute value (viscosity half-life). The control (Example 19A) consisted of sodium hyaluronate. The results are in Table 4.

TABLE 4

Ferric Chloride/Ascorbic Acid Test of Anhydride-Crosslinked Hyaluronic Acid

| Example Number | Dianhydride | Viscosity Half-Life |
|---|---|---|
| 19A | — | 0.9 hours |
| 19B | BTDA | 6 |
| 19C | PMDA | 24 |

EXAMPLE 20

This example describes crosslinking the methyltricaprylylammonium salt of hyaluronic acid with a polyanhydride.

The polyanhydride:

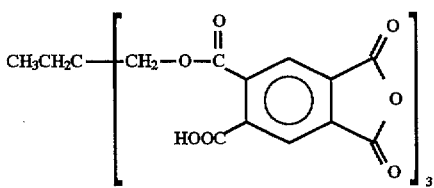

was prepared by mixing a solution of 0.1 g (1 meq) of 1,2,4,5-benzene tetracarboxylic acid dianhydride and 0.020 g (0.45 meq) of 2-ethyl-2-hydroxymethyl-1,3-propane diol in 10 ml of N-methylpyrrolidinone. The solution of the polyanhydride was then added to a solution of 0.7 g of the product of Example 1 in 100 ml of N-methylpyrrolidinone. After 1 hour, the solution became a dispersed gel with visible gel particles.

EXAMPLE 21

This example describes crosslinking the methyltricaprylylammonium salt of hyaluronic acid with a polyanhydride.

The polyanhydride:

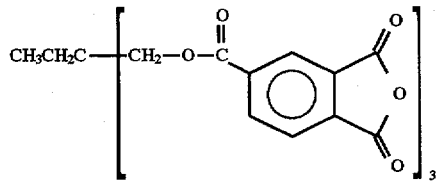

was prepared by mixing a solution of 0.1 g (1 meq) of trimellitic anhydride acid chloride, 0.1 g (0.45 meq) of 2-ethyl-2-hydroxymethyl-1,3-propane diol and 0.07 g of triethylamine in 10 ml of N-methylpyrrolidinone. The solution of the polyanhydride was then added to a solution of 0.7 g of the product of Example 1 in 100 ml of N-methylpyrrolidinone. After 1 hour, the solution became a dispersed gel with visible gel particles.

While the invention has been described with respect to specific embodiments, it should be understood that they are not intended to be limiting and that many variations and modifications are possible without departing from the scope of this invention.

What is claimed is:

1. A crosslinked composition comprising linked hyaluronic acid or salts thereof wherein at least one hydroxyl group of each linked hyaluronic acid or salt thereof is esterified with a carboxyl group contained in a monomeric polycarboxylic acid having at least four carboxyl groups, wherein at least two carboxyl groups of the polycarboxylic acid are esterified with hydroxyl groups of the polysaccharides, and wherein said crosslinked composition has substantially greater resistance to the enzyme hyaluronidase or to hydroxyl radicals than does hyaluronic acid or salts thereof.

2. The crosslinked composition of claim 1 comprising linked salt of hyaluronic acid wherein the salt is a salt of an alkali or alkaline earth metal, aluminum or ammonium.

3. The crosslinked composition of claim 1 comprising linked sodium salt of hyaluronic acid.

4. The crosslinked composition of claim 1 wherein the polycarboxylic acid is tetracarboxylic acid selected from the group consisting of 3,4,3',4'-benzophenone tetracarboxylic acid, 2,3,6,7-naphthalene tetracarboxylic acid, 1,4,5,8-naphthalene tetracarboxylic acid, 1,2,4,5-naphthalene tetracarboxylic acid, 1,2,5,6-naphthalene tetracarboxylic acid, 3,4,3'4'-diphenyl tetracarboxylic acid, 2,3,2',3'-diphenyl tetracarboxylic acid, 2,2-bis(3,4-dicarboxyphenyl)propane, 3,4,9,10-perylene tetracarboxylic acid, bis(3,4-dicarboxyphenyl)ether, 1,1-bis(2,3-dicarboxyphenyl) ethane, bis(3,4-dicarboxyphenyl)methane, decahydronaphthalene-1,4,5,8-tetracarboxylic acid, 4,8-dimethyl-1,2,3,4,5,6,7-hexahydronaphthalene-1,2,5,6-tetracarboxylic acid, pyromellitic acid, 2,6-dichloronaphthalene-1,4,5,8-tetracarboxylic acid, cyclopentane tetracarboxylic acid, pyrrolidine-2,3,4,5-tetracarboxylic acid, pyrazine-2,3,5,6-tetracarboxylic acid, thiophene-2,3,4,5-tetracarboxylic acid, ethylenediamine tetraacetic acid, diethylenetriamine pentaacetic acid, 4,4-sulfonyldiphthalic acid and 1-(3,4-dicarboxyphenyl)-1,3,3-trimethylindane-5,6(6,7)-dicarboxylic acid, 2,2'-bis(2,3-dicarboxyphenyl)propane, 1,1'-bis(3,4-dicarboxyphenyl) ethane, 1-(3'4-dicarboxyphenyl)-3-methylindane-5,6(6,7)-dicarboxylic acid, 3,4-dicarboxy-1,2,3,4-tetrahydro-1-naphthalenesuccinic acid, 1-methyl-3,4-dicarboxy-1,2,3,4-tetrahydro-1-naphthalenesuccinic acid, 3,4,9,10-perylene tetracarboxylic acid, 1,8,9,10-phenanthrene tetracarboxylic acid, 2,6-dichloronaphthalene-1,4,5,8-tetracarboxylic acid, 2,7-dichloronaphthalene-1,4,5,8-tetracarboxylic acid, 2,3,6,7-tetrachloronaphthalene-1,4,5,8-tetracarboxylic acid, 2,3,3',4'-benzophenone tetracarboxylic acid, 2,3,2',3'-benzophenone tetracarboxylic acid, 4,4'-oxodiphthalic acid, 3,3'-oxodiphthalic acid, 4,4'-thiodiphthalic acid, 3,3'-thiodiphthalic acid and 2,3,5,6-bicyclo(2,2,2)octane tetracarboxylic acid.

* * * * *